(12) United States Patent
DiMauro et al.

(10) Patent No.: US 8,167,920 B2
(45) Date of Patent: May 1, 2012

(54) INTRANASAL DELIVERY OF COMPOUNDS THAT REDUCE INTRANCRANIAL PRESSURE

(75) Inventors: Thomas M. DiMauro, Raynham, MA (US); Mohamed Attawia, Holmdel, NJ (US); Sean Lilienfeld, Raynham, MA (US); Terri A. Kapur, Sharon, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 1392 days.

(21) Appl. No.: 11/552,201

(22) Filed: Oct. 24, 2006

(65) Prior Publication Data

US 2007/0098645 A1    May 3, 2007

(51) Int. Cl.
*A61N 5/06* (2006.01)
(52) U.S. Cl. .......................................... 607/88; 128/898
(58) Field of Classification Search .................. 128/898; 606/88–94
See application file for complete search history.

(56) References Cited

U.S. PATENT DOCUMENTS

| | | | |
|---|---|---|---|
| 2,227,422 A | 1/1941 | Boerstler | |
| 4,105,034 A | 8/1978 | Shalaby | |
| 4,130,639 A | 12/1978 | Shalaby | |
| 4,140,678 A | 2/1979 | Shalaby | |
| 4,141,087 A | 2/1979 | Shalaby | |
| 4,205,399 A | 6/1980 | Shalaby | |
| 4,208,511 A | 6/1980 | Shalaby | |
| 5,270,300 A | 12/1993 | Hunziker | |
| 5,331,969 A | 7/1994 | Silberstein | |
| 5,445,608 A | 8/1995 | Chen | |
| 5,464,929 A | 11/1995 | Bezwada | |
| 5,595,751 A | 1/1997 | Bezwada | |
| 5,597,579 A | 1/1997 | Bezwada | |
| 5,607,687 A | 3/1997 | Bezwada | |
| 5,618,552 A | 4/1997 | Bezwada | |
| 5,620,698 A | 4/1997 | Bezwada | |
| 5,640,978 A | 6/1997 | Wong | |
| 5,645,850 A | 7/1997 | Bezwada | |
| 5,648,088 A | 7/1997 | Bezwada | |
| 5,683,436 A * | 11/1997 | Mendes et al. | 607/88 |
| 5,698,213 A | 12/1997 | Jamiolkowski | |
| 5,700,583 A | 12/1997 | Jamiolkowski | |
| 5,707,396 A | 1/1998 | Benabid | |
| 5,728,396 A | 3/1998 | Peery | |
| 5,766,234 A | 6/1998 | Chen | |
| 5,769,878 A | 6/1998 | Kamei | |
| 5,800,478 A | 9/1998 | Chen | |
| 5,859,150 A | 1/1999 | Jamiolkowski | |
| 5,910,309 A | 6/1999 | Ullrich | |
| 5,957,960 A | 9/1999 | Chen | |

(Continued)

FOREIGN PATENT DOCUMENTS

RU    2200041    1/2004

(Continued)

OTHER PUBLICATIONS

Patricia Adam, Michael Stiffman, and Robert L. Blake, Jr, "A Clinical Trial of Hypertonic Saline Nasal Spray in Subjects With the Common Cold or Rhinosinusitis", Archives of Family Medicine, 1998 vol. 7, pp. 39-43.*

(Continued)

*Primary Examiner* — Henry M Johnson, III
(74) *Attorney, Agent, or Firm* — Thomas M. DiMauro

(57) ABSTRACT

Increasing intranasal lymphatic circulation as a means of decreasing intracranial pressure in traumatic brain injury.

11 Claims, 5 Drawing Sheets

U.S. PATENT DOCUMENTS

| | | | |
|---|---|---|---|
| 5,995,857 | A | 11/1999 | Toomim |
| 6,083,919 | A | 7/2000 | Johnson |
| 6,358,272 | B1 * | 3/2002 | Wilden ............................ 607/89 |
| 6,365,726 | B1 | 4/2002 | Ballinger |
| 6,416,531 | B2 | 7/2002 | Chen |
| 6,418,344 | B1 | 7/2002 | Rezai |
| 6,527,782 | B2 | 3/2003 | Hogg |
| 6,537,304 | B1 | 3/2003 | Oron |
| 6,551,346 | B2 * | 4/2003 | Crossley ......................... 607/88 |
| 6,576,000 | B2 | 6/2003 | Carrison |
| 6,607,522 | B1 | 8/2003 | Hamblin |
| 6,610,713 | B2 | 8/2003 | Tracey |
| 6,713,246 | B1 | 3/2004 | Reinecke |
| 6,736,837 | B2 | 5/2004 | Fox |
| 6,921,413 | B2 | 7/2005 | Mahadevan Jansen |
| 7,081,128 | B2 | 7/2006 | Hart |
| 7,107,996 | B2 | 9/2006 | Ganz |
| 7,303,578 | B2 | 12/2007 | De Taboada |
| 7,351,253 | B2 * | 4/2008 | DiMauro et al. ................ 607/88 |
| 7,435,252 | B2 * | 10/2008 | Krespi et al. ................... 607/88 |
| 2001/0047195 | A1 * | 11/2001 | Crossley ......................... 607/88 |
| 2001/0051766 | A1 | 12/2001 | Gazdzinski |
| 2002/0029071 | A1 | 3/2002 | Whitehurst |
| 2002/0087206 | A1 | 7/2002 | Hirschberg |
| 2002/0103429 | A1 | 8/2002 | deCharms |
| 2002/0122621 | A1 | 9/2002 | Li |
| 2003/0097122 | A1 | 5/2003 | Ganz |
| 2003/0167080 | A1 | 9/2003 | Hart |
| 2003/0216797 | A1 | 11/2003 | Oron |
| 2003/0236394 | A1 | 12/2003 | Schwarz |
| 2004/0018557 | A1 | 1/2004 | Qu |
| 2004/0030368 | A1 | 2/2004 | Kemeny |
| 2004/0049249 | A1 | 3/2004 | Rubery |
| 2004/0073278 | A1 * | 4/2004 | Pachys ............................ 607/88 |
| 2004/0116985 | A1 | 6/2004 | Black |
| 2004/0127892 | A1 | 7/2004 | Harris |
| 2004/0127961 | A1 | 7/2004 | Whitehurst |
| 2004/0219600 | A1 | 11/2004 | Williams |
| 2005/0107851 | A1 | 5/2005 | Taboada |
| 2005/0107853 | A1 * | 5/2005 | Krespi et al. ................... 607/89 |
| 2005/0175658 | A1 | 8/2005 | DiMauro |
| 2005/0228291 | A1 | 10/2005 | Chance |
| 2006/0004317 | A1 | 1/2006 | Mauge |
| 2006/0155348 | A1 | 7/2006 | deCharms |
| 2006/0167531 | A1 | 7/2006 | Gertner |
| 2006/0276861 | A1 * | 12/2006 | Lin ................................. 607/89 |
| 2006/0287695 | A1 * | 12/2006 | DiMauro et al. ................ 607/88 |
| 2007/0010859 | A1 * | 1/2007 | DiMauro et al. ................ 607/94 |
| 2007/0239235 | A1 | 10/2007 | DiMauro |

FOREIGN PATENT DOCUMENTS

| | | |
|---|---|---|
| RU | 2222362 | 1/2004 |

OTHER PUBLICATIONS

Narrow-Band Red Light Phototherapy in Perennial Allergic Rhinitis and Nasal Polyposis Original Research Article Annals of Allergy, Asthma & Immunology, vol. 78, Issue 4, Apr. 1997, pp. 399-406; Ittai Neuman, Yehuda Finkelstein.*

Aleksandrova, "Increased level of beta-amyloid in the brain of bulbectomized mice", Biochemistry, Feb. 2004, pp. 176-80, vol. 69(2)—abstract.

Aliev, "Atherosclerotic lesions and mitochondria DNA deletions in brain microvessels as a central target for the development of human AD and AD-like pathology in aged transgenic mice", Ann NY Acad. Sci., Nov. 2002, pp. 45-64, vol. 977—abstract.

Aliev, "Mitochondria and vascular lesions as a central target for the development of Alzheimers disease and Alzheimers like pathology in transgenic mice", Neurological Research, Sep. 2003, pp. 665-674, vol. 25(6)—abstract.

Allcock, "Polyphosphazenes", The Encyclopedia of Polymer Science, 1988, pp. 31-41, vol. 13, Wiley Intersciences, John Wiley & Sons.

Anders, "Low power laser irradiation alters the rate of regeneration of the rat facial nerve", Lasers Surg Med., 1993, pp. 72-82, vol. 13(1)—abstract.

Anders, "Phototherapy promotes regeneration and functional recovery of injured peripheral nerve", Neurological Research, Mar. 2004, pp. 233-239, vol. 26.

Bachis, "Interleukin-10 Prevents Glutamate-Mediated Cerebellar Granule Cell Death by Blocking Caspase-3-Like Activity", J. Neuroscience, May 1, 2001, pp. 3104-3112, 21(9), society of Neuroscience.

Balaban, "He-Ne laser irradiation of single identified neurons", Lasers Surg Med, 1992, pp. 329-337, vol. 12(3), abstract.

Balasingam, "Attenuation of Astroglial Reactivity by Interleukin-10", J. Neuroscience, May 1, 1996, pp. 2945-2955, vol. 16(9), Society for Neuroscience.

Bhardwaj, "Hypertonic Saline Worsens Infarct Volumn After Transient Focal Ischemia in Rats Editorial Comment", Stroke, 2000, vol. 31, pp. 1694-1701, American Heart Association.

Brennan, "Interleukin 10 and Arthritis", Rheumatology, 1999, pp. 293-297, vol. 38. , British Society for Rheumatology.

Brodie, Differential Effects of Th1 and Th2 Derived Cytokines on NGF Synthesis by Mouse Astrocytes, FEBS Lett., 1996, pp. 117-120, vol. 394(2), Federation of Eurpoean Biochemical Societies.

Brown et al., "Gelatin/Chondroitin 6-Sulfate Misrospheres For the Delivery of Therapeutic Proteins to the Joint", Arthritis. Rheum. Dec. 1998; pp. 2185-2195, vol. 41(12), American College of Rheumatology.

Burkoth, "A Review of Photocrosslinked Polyanhydrides: in situ Forming Degradable Networks", Biomaterials, 2000, pp. 2395-2404. vol. 2, Elsevier Science Ltd.

Byrnes, "Light Promotes Regeneration and Functional Recovery and Alters the Immune Response After Spinal Cord Injury", Lasers in Surgery and Medicine, 2005, pp. 1-15, vol. 9999.

Chen, "Effects of light beam size on fluence distribution and depth of necrosis in superficially applied photodynamic therapy of normal rat brain", Photochem Photobiol., Sep. 1992, pp. 379-384, vol. 56(3)-abstract.

Cho, "Effect of low-level laser therapy on osteoarthroplasty in rabbit", In Vivo, 2004, Sep.-Oct. pp. 585-591, vol. 18(5)—abstract.

Cohn and Younes, "Biodegradable PEO/PLA block copolymers", Journal of Biomaterials Research,1988, pp. 993-1009, vol. 22, John Wiley and Sons.

Cohn, Polymer Preprints, Biomaterials Research Laboratory, (ACS Division of Polymer Chemistry), 1989, p. 498, vol. 30(1),(e.g. PEO/PLA).

Cottrell, Mitochondrial enzyme-deficient hippocompal neurons and choroidal cells in AD., Neurology, Jul. 2001, pp. 260-264, vol. 57(2)—abstract.

Cottrell, "The role of cytochrome c oxidase deficient hippocampal neurons in Alzheimer's disease", Neuropathol Appl Neurobiol., Oct. 2002, pp. 390-396, vol. 28(5)—abstract.

Davies, "Axonal loss from the olfactory tracts in Alzheimer's disease", Neurobiol Aging., Jul.-Aug. 1993, pp. 353-7, vol. 14(4) —abstract.

Del Bo, "Reciprocal control of inflammatory cytokines, IL-1 and IL-6, and beta-amyloid production in cultures", Neurosci Lett., Mar. 1995, pp. 70-74, vol. 188(1)—abstract.

Dugan, "Fullerene-based antioxidants and neurodegenerative disorders", Parkin. Relat. Disord., 1002, Jul., pp. 243-246 , vol. 7 (3)., Elsevier Sciene Ltd.

Ebadi, "Peroxynitrite and mitochondrial dysfunction in the pathogenesis of Parkinson's disease", Antioxidants & Redox Signaling, 2003, pp. 319-335, vol. 5(3), Mary Ann Liebert, Inc.

EELS, "Mitochondrial signal transduction in accellerated wound and retinal healing by near-infrared light therapy", Mitochondrion, 2004, pp. 559-567, vol. 4, Elsevier B.V.

Elias, "Hyperthermia from interstitial laser irradiation in normal rat brain", Lasers Surg Med., 1987, pp. 370-5, vol. 7(4)—abstract.

Giuliani, "Very low level laser therapy attenuates edema and pain in experimental models", Int J Tissue React., 2004, pp. 29-37, vol. 26(1-2)—abstract.

Gonzalez, "Protection against MPP+ neurotoxicity in cerebellar granule cells by antioxidants", Cell Biology Int'l, (2004) pp. 373-80, vol. 28, Elsevier.

Gorbatenkova, "Reactivation of superoxide dismutase by the helium-neon laser irradiation", Biofizika, Jul.-Aug. 1988, pp. 717-9, vol. 33(4) —abstract.

Gorbatenkova, "The red light of the helium-neon laser reactivates superoxide dismutase", Biull Eksp Biol Med., Mar. 1989, pp. 302-305, vol. 107(3)—abstract.

Grilli, "Interleukin-10 modulates neuronal threshold of vulnerability to ischaemic damage", Eur. J. Neuroscience, Jul. 2000, pp. 2265-2272, 12(7), Federation of European Neuroscience Societies.

Haas, "Inducible nitric oxide synthase and argininosuccinate synthetase: co-induction in brain tissue of patients with Alzheimer's dementia and following stimulation with beta-amyloid 1-42 in vitro", Neurosci Lett., Apr. 5, 2002, pp. 121-5, vol. 322(2)—abstract.

Hallam, "An investigation of the effect of tacrine and physostigmine on spatial working memory deficits in the olfactory bulbectomised rat", Behav Brain Res., Aug. 31, 2004, pp. 481-6, vol. 153(2)—abstract.

Hart, "Comparison of the Suppressive Effects of Interleukin-10 and Interleukin-4 on Synovial Fluid Macrophages and Blood Monocytes From Patients With Inflammatory Arthritis", Immunology, 1995, Apr., pp. 536-42, vol. 84(4).

Hebeda, "Light Propagation in the Brain Depends on Nerve Fiber Orientation Experimental Study", Neurosurgery, Oct. 1994, pp. 1992-1998, vol. 35(4).

Heller, "Development of Poly(Ortho Esters)", Handbook of Biodegradable Polymers, 1997, pp. 99-118, Hardwood Academic Press.

Hozumi, "Characteristics of changes in cholinergic function and impairment of learning and memory-related behavior induced by olfactory bulbectomy", Behav Brain Res., Jan. 2003, pp. 9-15, vol. 138(1)—abstract.

Huell, "Interleukin-6 is present in early stages of plaque formation and is restricted to the brains of Alzheimer's disease patients", Acta Neuropathol (Berl), 1995, pp. 544-551, vol. 89(6)—abstract.

Iakymenko, "Regulatroy role of low-intensity laser radiation on the status of antioxidant system", Ukr. Biokhim Zh., Jan.-Feb. 2001, pp. 16-23, vol. 73(1)—abstract.

Itoh, "Defects of Cytochrome c Oxidase in the Substantia Nigra of Parkinson's Disease: An Immunohistochemical and Morphometric Study", Mov. Disord., 1997, Jan. pp. 9-16, vol. 12(1), Movement Disorder Society.

Ji, "Interstitial photoradiation injury of normal brain", Lasers Surg Med, 1992, pp. 425-431, vol. 12(4)—abstract.

Johanson, "Choroid Plexus Recovery After Transient Forebrain Ischemia: Role of the Growth Factors and Other Repair Mechanisms", Cell. Mol. Neurobiol., 2000, pp. 197-216, vol. 20(2), Plenum Publishing Corp.

Kamanli, "Plasma lipid peroxidation and antioxidant levels in patients with rheumatoid arthritis", Cell Biochem Funct., Jan-Feb 2004, pp. 53-7, vol. 22(1)—abstract.

Kang, "CD11 b+ Macrophages That Infiltrate Human Epidermis After In Vivo Ultraviolet Exposure Potently Produce IL-10 and Represent the Major Secretory Source of Epidermal L-10 Protein", J. Immunol., 1994, pp. 5256-5264, vol. 153, The American Association of Immunologists.

Karu, "Suppression of Human Blood Chemiluminescence by Diode Laser Irradiation at Wavelengths 660, 820, 880 or 950 nm", Laser Ther. 1993, pp. 103-109, vol. 5, John Wiley and Sons.

Kelly, "The Anti-inftammatory Cytokin, Interleukin (IL)-10, Blocks the Inhibitory Effect of IL-1B on Long Term Potentiation", J. Biol. Chem., 2001, pp. 45564-72, vol. 276(49), JBC Papers in Press.

Kemnitzer and Kohn, "Degradable polymers derived from the amino acid L-Tyrosine", the Handbook of Biodegradable Polymers, 1997, pp. 251-272 Hardwood Academic Press.

Klebanov, "Effect of low intensity laser light in the red range on macrophages superoxide dismutase activity", Biofizika, May-Jun. 2003, pp. 462-473, vol. 48(3)—abstract.

Knoblach, "Interleukin-10 Improves Outcome and Alters Proinflammatory Cytokins Expression After Experimental Traumatic Brain Injury", Exp. Neuro., 1998, pp. 143-151, vol. 153, Academic Press.

Koh, "Development of cerebrospinal fluid absorption sites in the pig and rat" Anat. Embryol (Berl), 2006 Mar.10 (e-pub).

Koh, "Integration of the subarachnoid space and lymphatics: Is it time to embrace a new concept of cerebrospinal fluid absorption?" Cerebrospinal Fluid Research, 2005, 2:6, pp. 1-11, Biomed Central Ltd.

Konchugova, "Immunodepressive effect of transcerebral lasers", Biull Eksp Biol Med., Apr. 1993, pp. 391-393, vol. 115(4)—abstract.

Kovacs, "Beta-amyloid deposition and neurofibrillary tangle formation in the olfactory bulb in ageing and Alzheimer's disease", Neuropathol Appl Neurobiol., Dec. 1999, pp. 481-91, vol. 25(6)—abstract.

Kovacs, "Olfactory centres in Alzheimer's disease: olfactory bulb is involved in early Braak's stages", Neuroreport., Feb. 2001, pp. 285-288, vol. 12(2)—abstract.

Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Lasers in Surgery and Medicine, 2002, pp. 283-288, vol. 31, Wiley-Liss.

Lio, "Interleukin-10 promoter polymorphism in sporadic Alzheimer's disease, Genes Immun.", 2003, pp. 234-238, vol. 4., Nature Publishing Group.

Louin, "Selective inhibition of inducible nitric oxide synthase reduces neurological deficit but not cerebral edema following traumatic brain injury", Neuropharmacology, 2006, Feb. 50(2) 182-90, Elsevier.

Mann, "Alzheimer's disease: an olfactory connection?", Mech Ageing Dev., Jan. 1099, pp. 1-15, vol. 42(1)—abstract.

Mark,"Hydrogels", Concise Encyclopedia of Polymer Science and Engineering, 1990, pp. 458-459, Wiley and Sons.

Mochizuki-Oda, "Effects of near-infra-red laser irradiation on adenosine triphosphate and adenosine diphosphate contents of rat brain tissue", Neuroscience Letters, 2002, pp. 207-210, vol. 323, Elsevier.

Nagra, "Quantification of cerebrospinal fluid transport across the cribriform plate into lymphatics of rats", Am./.Physiol. Regul. Integr. Compo Physiol. Jun. 22, 2006 (e-pub).

Nakao, "Overexpressing Cu/Zn superoxide dismutase enhances survival of transplanted neurons in a rat model of Parkinson's disease", Nat. Med. 1995, Mar., pp. 226-231 vol. (3), Nature Medicine.

Neuman, Narrow-band red light phototherapy in perennial allergic rhinitis and nasal polyposis, Annals of Allergy, Asthma, & Immunology, Apr. 1997, pp. 399-406, vol. 78.

Nowak, "The Effect of Superpulsed Carbon Dioxide Laser Energy on Keloid and Normal Dermal Fibroblast Secretion of Growth Factors: A Serum-Free Study, Plast. Reconstr. Surg.", 2000, pp. 2039-48, vol. 105(6). Stanford Univ. Medical Center.

Ostrakhovich, "Active forms of oxygen and nitrogen in blood cells of patients with rheumatoid arthritis: effect of laser therapy", Vestn Ross Akad Med Nauk. 2001, pp. 23-7, vol. 5.—abstract.

Powers, "Light dosimetry in brain tissue: an in vivo model applicable to photodynamic therapy, Lasers Surg Med.", 1986, pp. 318-322, vol. 6(3)—abstract.

Prehn, "Protective Effect of Transforming Growth Factor-B1 on B-Amyloid Neurotoxicity in Rat Hippocampal Neurons, Mol. Pharm.", Feb. 1996, pp. 319-328, vol. 49(2), The American Society for Pharmacology and Experimental Therapeutics.

Qiu, "Interleukin-6, beta-amyloid peptide and NMDA interactions in rat cortical neurons", J Neuroimmunol, 2003, pp. 51-57, vol. 139(1-2)—abstract.

Ren, "Transforming Growth Factors-B Protect Primary Rat Hippocampal Neuronal Cultures From Degeneration Induced by B-amyloid Peptide", Brain. Res., 1996, Sep. 2, pp. 16-24, vol. 732 (1-2), Elsevier Science BV.

Rivas, "Systemic Suppression of Delayed-Type Hypersensitivity by Supernatants From UV-Irradiated Keratinocytes", J. Immun, Dec. 15, 1992, pp. 3865-3871, vol. 149(12), The American Association Immunologists.

Romm, "Action of laser radiation on the peroxide chemiluminescence of wound exudates", Biull Eksp Biol Med., Oct. 1986, pp. 426-8, vol. 102(10)—abstract.

Sawada, "Interleukin-10 Inhibits Both Production of Cytokines and Expressoin of Cytokine Receptors in Microglia", J. Neurochemistry, 1999, pp. 1466-1471, vol. 72, Lippincott Williams & Wilkins.

Schindl, "Low-Intensity Laser Therapy: A Review", Journal of Investigative Medicine, Sep. 2000, pp. 312-326, vol. 48(5).

Schmidt, "Evaluation of Photodynamic Therapy Near Functional Brain Tissue in Patients With Recurrent Brain Tumors", Journal of Neurooncology, 2004, pp. 201-207, vol. 67, Kluwer Academic Publishers, The Netherlands.

Schmitt, "Exposure to Ultraviolet Radiation Causes Dendritic Cells/Macrophages to Secrete Immune-Suppressive IL-12p40 Homodimers", J. Immunology, 2000, pp. 3162-7, vol. 165, The American Association of Immunologists.

Schwarz, "Effects of hypertonic (10%) saline in patients with raised intracranial pressure after stroke" Stroke, 2002, 33, pp. 136-140, American Heart Association.

Serot, "A Cytokine Cascade Including Prostaglandin E2, IL-4 and IL-10 Is Responsible for UV-Induced Systemic Immune Suppression", J. Neuroimmunology, 2000, pp. 115-119, vol. 104, Elsevier Science B.V.

Shirasawa, "Physiological roles of endogenous nitric oxide in lymphatic pump activity of rat mesenery in vivo" Am. J. Physiol. Gastrointest. Liver Physiol., 2000, pp. G551-G556, vol. 278, The American Physiological Society.

Shreedhar, "A CylOkine Cascade Including Prostaglandin E2, IL-4 and IL-10 Is Responsible for UV-Induced Systemic Immune Suppression", J. Immunol., 1998, pp. 3783-3789, vol. 160, The American Association of Immunologists.

Snyder, "Quantitation of Calcitonin Gene-Related Peptide mRNA and Neuronal Cell Death in Facial Motor Nuclei Following Axotomy and 633 nm Low Power Laser Treatment", Lasers in Surgery and Medicine, 2002, pp. 216-222, vol. 31, Wiley-Liss, Inc.

Sohrabji, "Local and cortical effects of olfactory bulb lesions on trophic support and cholingeric function and their modulation by estrogen", J Neurobiol, Nov. 2000, pp. 61-74, vol. 45(2)—abstract.

Strle, IL-10 Promotes Survival of Microglia Without Activating Akt, J. Neuroimmunology, Jan. 2002; pp. 9-19, vol. 122(1-2).

Strle, "Interleukin-10 in the Brain, Crit. Rev.", Immunology, 2001, pp. 427- 449, vol. 21(5), Begell House.

Stutzmann, "GaN-based Heterostructures for Sensor Applications", Diamond and Related Materials, 2002, pp. 886-891, vol. 11, Elsevier Science BV.

Sutton, "Amyloid-B peptide induced inflammatory reaction is mediated by the cytokines tumor necrosis factor and interleukin-1", J. Submicrosc.Cytol. Pathol., 1999, pp. 313-323, vol. 31(3), Elsevier Science B.V.

Szczepanik, "Il-4, IL-10 and IL-13 Modulate AB)1-42)-Induced Cytokine and Chemokine Production in Primary Murine Microglia and a Human Monocyte Cell Line", J. Neuroimmunology, 2001, pp. 49-62, vol. 113, Elsevier Science B.V.

Town, "Reduced Th1 and Enhanced Th2 Immunity with Alzheimer's B-amyloid 1-42", J. Neuroimmunol., (2002), pp. 49-89, vol. 132, Elsevier Science BV.

Tsuboi, "Tau pathology in the olfactory bulb correlates with Braak stage, Lewy body pathology and apolipoprotein epsilon4", Neuropathol Appl Neurobiol., Oct. 2003, pp. 503-510, vol. 5—abstract.

Unterberg, "Edema and Brain Trauma", Neuroscience, 2004, 1021-1029, vol. 129, Elsevier Ltd.

Vandorpe, "Biodegradable Polyphosphazenes for Biomedical Applications", Handbook of Biodegradable Polymers, 1997, pp. 161-182, Hardwood Academic Press.

Vink, "Novel therapies in development for the treatment of traumatic brain injury", Exp. Op. Invest. Drugs, Oct. 2002, pp. 1375-86, vol. 11(1), Ashley Publications Ltd.

Vink, "Recent advances in the development of multifactorial therapies for the treatment of traumatic brain injury", Exp. Op. Invest. Drugs, 2004, pp. 1263-1274, vol. 13(10), Ashley Publications Ltd.

Vitreshchak, "Laser modification of the blood in vitro and in vivo in patients with parkinson's disease", Bull. Exp. Biol. Med., May 2003, pp. 403-432, vol. 135(5), Plenum Publishing Corporation.

Vladimirov, "Molecular and cellular mechanisms of the low intensity laser radiation effect", Biofizika, Mar.-Apr. 2004, pp. 339-350, vol. 49(2)—abstract.

Vladimirov, Photobiological Principles of Therapeutic Applications of Laser Radiation Biochemistry, 2004, pp. 81-90, vol. 69(1), Vladimirov, Osipov, Klebanov.

Vladimirov, "Photoreactivation of superoxide dismutase by intensive red (Laser) light", Free Radical Biology & Medicine, 1988, pp. 281-286, vol. 5, Pergamon Press.

Volotovskaia, "Antioxidant action and therapeutic efficacy of laser irradiation blood in patients with ischemic heart disease", Vopr Kurortol Lech Fiz Kult, May-Jun. 2003, pp. 22-25, vol. 3—abstract.

Von Der Weid, "Nitric oxide decreases pacemaker activity in lymphatic vessels of guinea pig messentry", Am. J. Physiol. Heart Circ. Physiol., 2001, Jun: 280(6) H2707-16, The American Physiology Society.

Walicke, "Purification of a human red blood cell protein supporting the survival of cultured CNS neurons and its identification as catalase", J. Neuroscience, Apr. 1986, pp. 1114-1121, vol. 6(4), Society for Neuroscience.

Wollman, "In vitro cellular processes sprouting in cortex microexplants of adult rat brains induced by low power laser irradiation", Neurologic Research, Jul. 1998, pp. 470-472, vol. 20, Forefront Publishing Group.

Wollman, Low power laser irradiation enhances migration and neurite sprouting of cultured rat embryonal brain cells, Neurological Research, Oct 1996, pp. 467-470, vol. 18, Forefont Publishing Group.

Wong-Riley, Light-emitting diode treatment reverses the effect of TTX on cytochrome osidase in neurons, Neuroreport, Oct. 8, 2001, pp. 3033-3037, vol. 12(14)—abstract.

Wong-Riley, Photobiomodulation directly benefits primary neurons functionally inactivated by toxins: role of cytochrome c oxidase, J. Biol. Chem. 2005, Feb. 11, pp. 4761-4771, 280(6), Epub Nov. 22, 2004, American Society for Biochemistry and Molecular Biology, Inc.

Yamamoto, "Characteristics of memory dysfunction in olfactory bulbectomized rats and the effects of cholinergic drugs", Behav Brain Res, Feb. 1997, pp. 57-62, vol. 83(1-2)—abstract.

Yamamoto, Involvement of the olfactory system in learning and memory: a close correlation between the olfactory deficit and the course of Alzheimer's disease?, Yakubutsu Seishin Kodo, 1991, pp. 223-235, vol. 11(4)—abstract.

Yaroslavsky, Optical Properties of Selected Native and Coagulated human Brain Tissue In Vitro In the Visible and Near Infrared Spectral Range, Phys. Med. Biol., 2002, pp. 2059-2073, vol. 47, IOP Publishing.

Zawieja, "Inhibition of the active lymph pump in rat mesenteric lymphatics by hydrogen peroxide", Lymphology, 1993, Sep. 26(3) pp. 135-142—abstract.

Adam, "A Clinical Trial of Hypertonic Saline Nalas Spray in Subjects With the Common Cold or Rhinosinusitis", Archives of Family Medicine, 1998, vol. 7, pp. 39-43, American Medical Association.

Neuman, "Narrow-Band Red light Phototherapy in Perennial Allergic Rhinitis and Nasal Polyposis" Ann Allergy Asthma Immunol., Apr. 1997; pp. 399-406, vol. 78(4),—abstract.

* cited by examiner

FIG. 4A
FIG. 4B
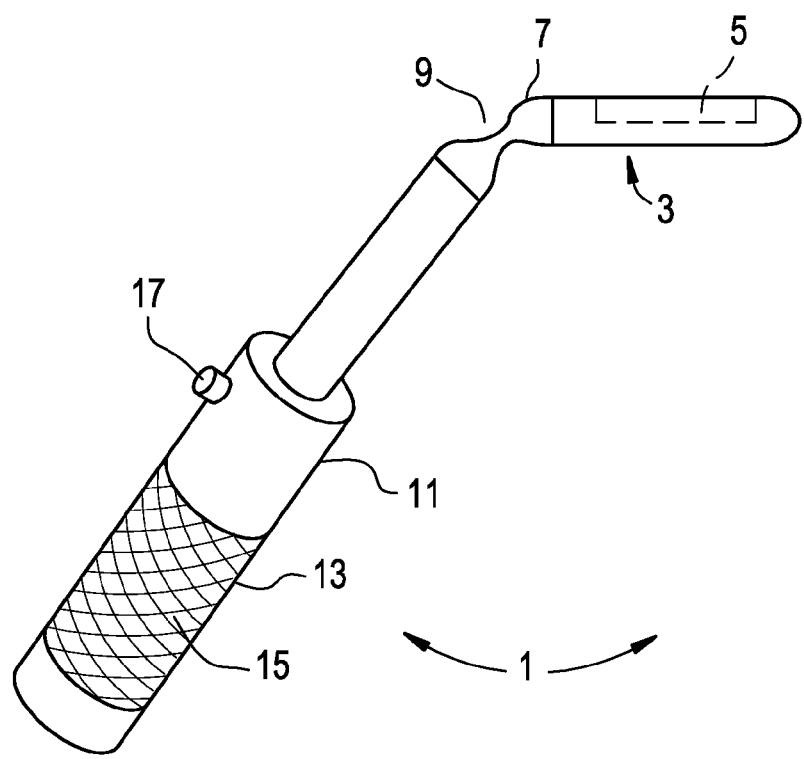
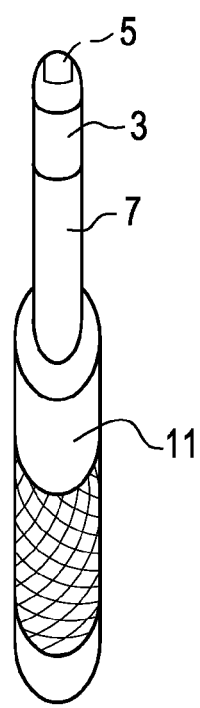

INTRANASAL DELIVERY OF COMPOUNDS THAT REDUCE INTRANCRANIAL PRESSURE

BACKGROUND OF THE INVENTION

According to Vink, *Exp. Op. Invest. Drugs*, October 2002, 11(1) 1375-86, and Vink, *Exp. Op. Invest. Drugs*, (2004) 13(10) 1263-74, "traumatic brain injury (TBI) is one of the leading causes of death and disability in the industrialized world and remains a major health problem with serious socio-economic consequences. In industrialized countries, the mean incidence of traumatic brain injury (TBI) that results in a hospital presentation is 250 per 100,000. In Europe and North America alone, this translates to more than 2 million TBI presentations annually. Approximately 25% of these presentations are admitted for hospitalization. Those individuals who survive TBI are often left with permanent neurological deficits, which adversely affect the quality of life and as a result, the social and economic cost of TBI is substantial. Despite the significance of these figures, there is no single interventional pharmacotherapy that has shown efficacy in the treatment of clinical TBI."

It is well known that TBI causes edema in the brain, thereby elevating intrancranial pressure (ICP). Unterberg, *Neuroscience*, 129, 2004, 1021-1029. According to Bhardwaj, *Stroke*, 2000, 31, 1694-1701, intravenous administration of osmotic agents susch as mannitol and hypertonic saline have potent anti-edema action, presumably by drawing water from interstitial and intracellular spaces into the intravascular compartment. However, the use of such agents remains controversial. For example, the long term beneficial effects of mannitol remain unknown. There is some evidence that repeated doses of mannitol may even aggravate brain edema. Lastly, mannitol fails to be effective in some patients, even after repeated doses. Schwarz, Stroke, 2002, 33, 136-140.

SUMMARY OF THE INVENTION

It is an object of the present invention to provide an alternative means for reducing intracranial pressure, in head injury or other states when intracranial pressure (ICP) is elevated, without the use of intravenous mannitol or hypertonic saline.

The present inventors have noted that a substantial fraction of intrancranial CSF is drained through the cribriform plate located at the top of the nasal cavity. Koh, *Cerebrospinal Fluid Research*, 2005, 2, 6 (2005) suggests the possibility that CSF may drain into extracranial lymphatic vessels in significant volumes. Koh further states that CSF mainly flows along the extensions of the subarachnoid compartment associated primarily with olfactory nerves, convects through the cribriform plate and is ultimately absorbed by the lymphatic tissue in the nasal mucosa.

It has further been reported that CSF is removed from the cranium by transport through the cribriform plate in associated with the olfactory nerves, and is then absorbed into lymphatics located in the submucosa of the olfactory epithelium (olfactory turbinates). Nagra, "Quantification of cerebrospinal fluid transport across the cribriform plate into lymphatics of rats", *Am. J. Physiol. Regul. Integr. Comp. Physiol.* 2006 Jun. 22 (e-pub).

It has further been reported that lymphatics encircle the olfactory nerve trunks on the extracranial surface of the cribriform plate and absorb CSF. Koh, "Development of cerebrospinal fluid absorption sites in the pig and rat", *Anat. Embryol (Berl)*, 2006 Mar. 10 (e-pub).

Therefore, the present inventors have undertaken efforts to develop inventions in which CSF drainage through the cribriform plate is enhanced. It is believed that enhancing CSF drainage through the cribriform plate will beneficially lower intracranial pressure (ICP) and thereby provide physiological benefit to the TBI patient.

The present inventors further believe that drainage through the cribriform plate can be enhanced by increasing the pumping activity of the lymphatic tissue present in the olfactory and nasal mucosa.

Therefore, in accordance with the present invention, there is provided a method of reducing intracranial pressure in a patient having a raised intracranial pressure comprising the steps of:

a) intranasally applying a therapeutic agent to an intranasal lymphatic vessel of the patient to increase lymphatic circulation.

In accordance with some embodiments of the present invention, there is provided a method of reducing intracranial pressure in a patient having a raised intracranial pressure (such as occurs in traumatic brain injury), comprising the steps of:

a) applying a formulation to intranasal lymphatic tissue in an amount effective to increase lymphatic circulation.

In accordance with some embodiments of the present invention, there is provided a method of treating a patient having a raised intracranial pressure, comprising:

a) irradiating a nasal lymphatic tissue of the patient with an effective amount of red light to increase lymphatic circulation.

DESCRIPTION OF THE FIGURES

FIGS. 4a-4c disclose side, front and upper views of a red light emitting intranasal device of the present invention.

DETAILED DECSRIPTION OF THE INVENTION

Figure 1:
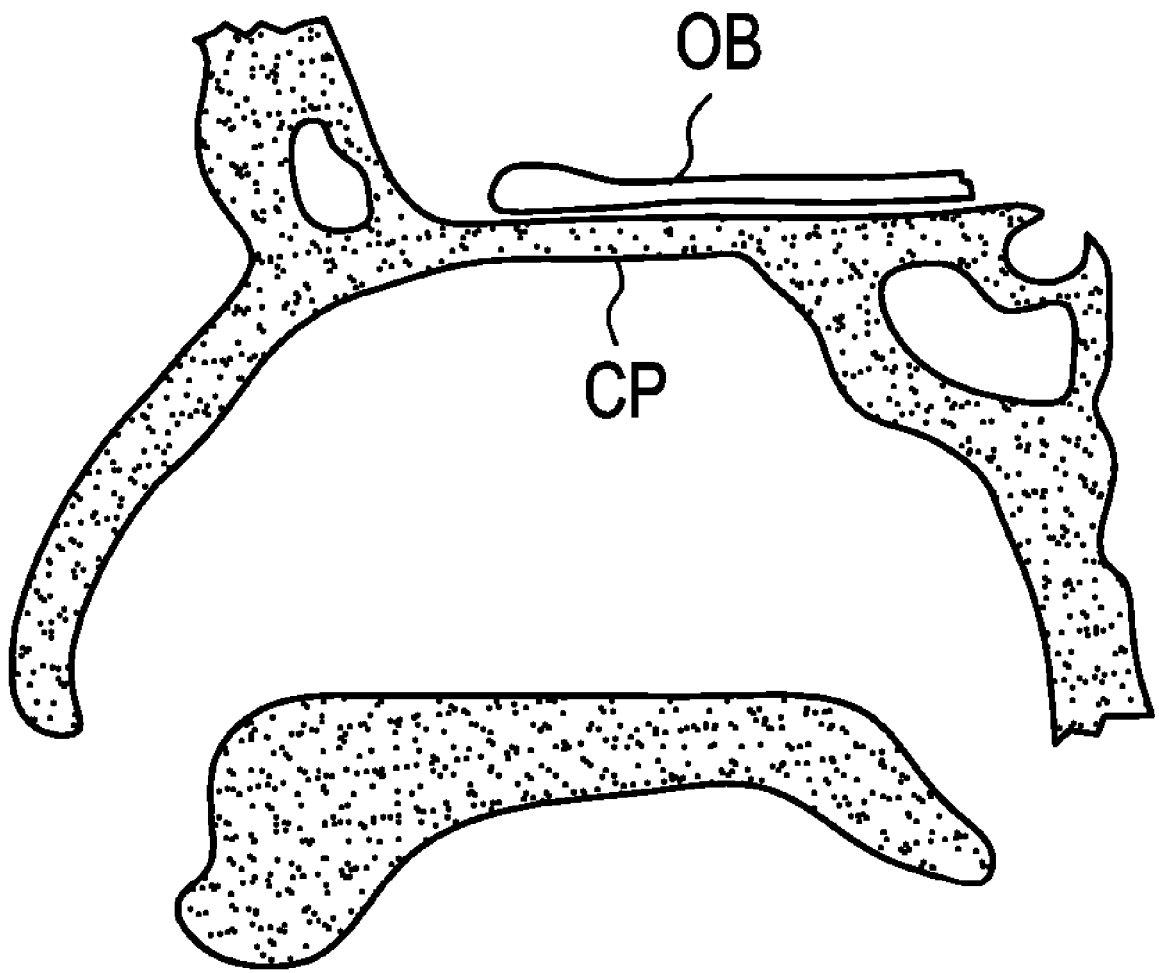
FIG. 1 discloses a cross-sectional side view of the nasal cavity, wherein the cribriform plate is a wafer-thin ledge of porous bony tissue.

Now referring to FIG. 1, the cribriform plate CP is a wafer-thin ledge of porous bony tissue located beneath the prefrontal cortex portion of the brain and above the nasal cavity. The porosity of the cribriform plate is filled with olfactory nerves extending from the olfactory bulb OB (located at the lower base of the brain) and terminating within the nasal mucosa. As shown here, the cribriform plate has a thickness of about 1 mm while the olfactory bulb has a thickness of about 3 mm. Thus, red light will traverse 1 mm of nerve fiber tissue within the cribriform plate and 3 mm of grey matter associated with the olfactory bulb, totaling to about 4 mm.

Figure 2:
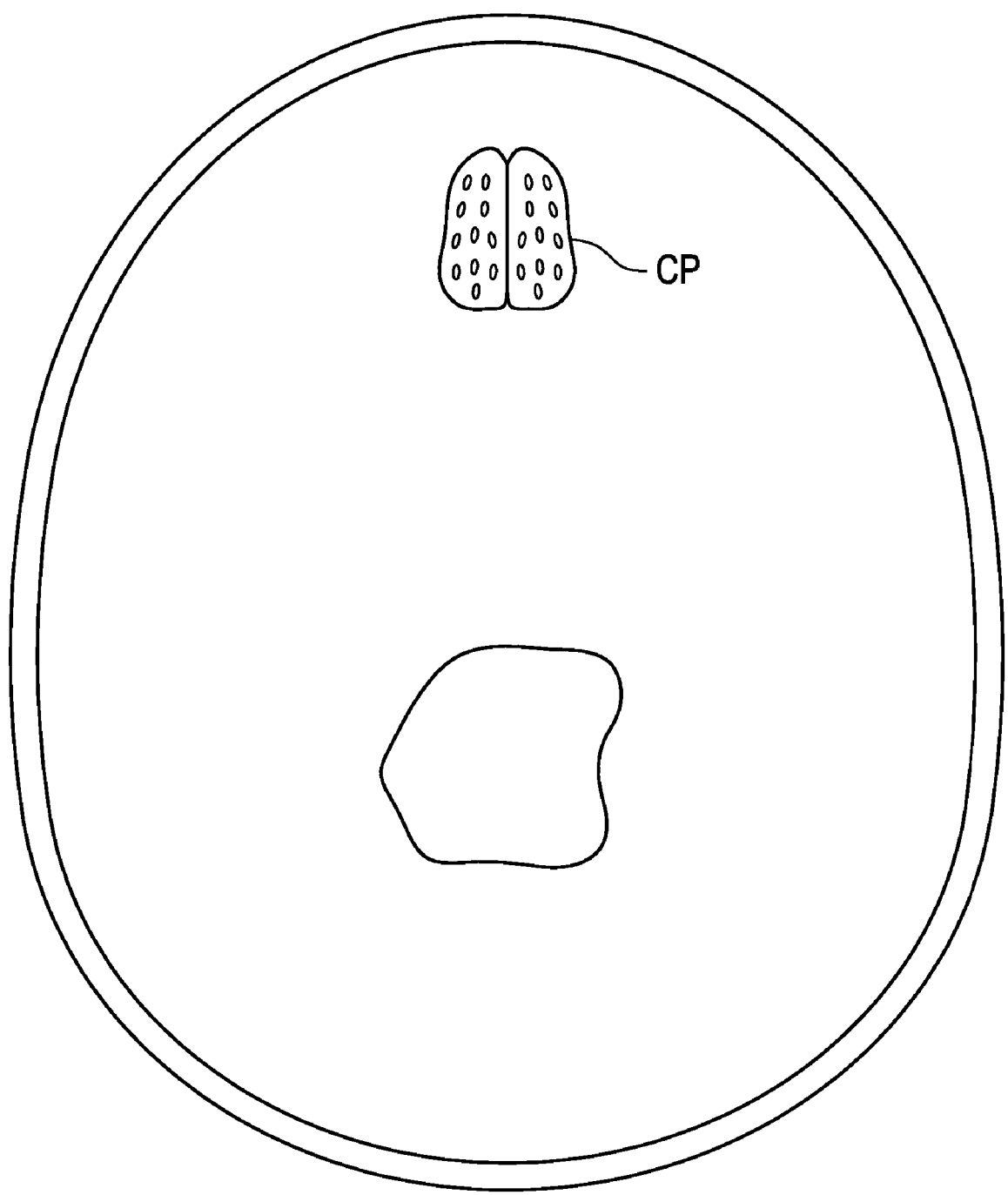
FIG. 2 discloses a coronal view of the cribriform plate.

Now referring to FIG. 2, the coronal view of the cribriform plate CP reveals that fairly large throughholes extend transversely through about one-half of the cribriform plate. These throughholes comprises about 50 areal % of the cribriform plate.

Figure 3:
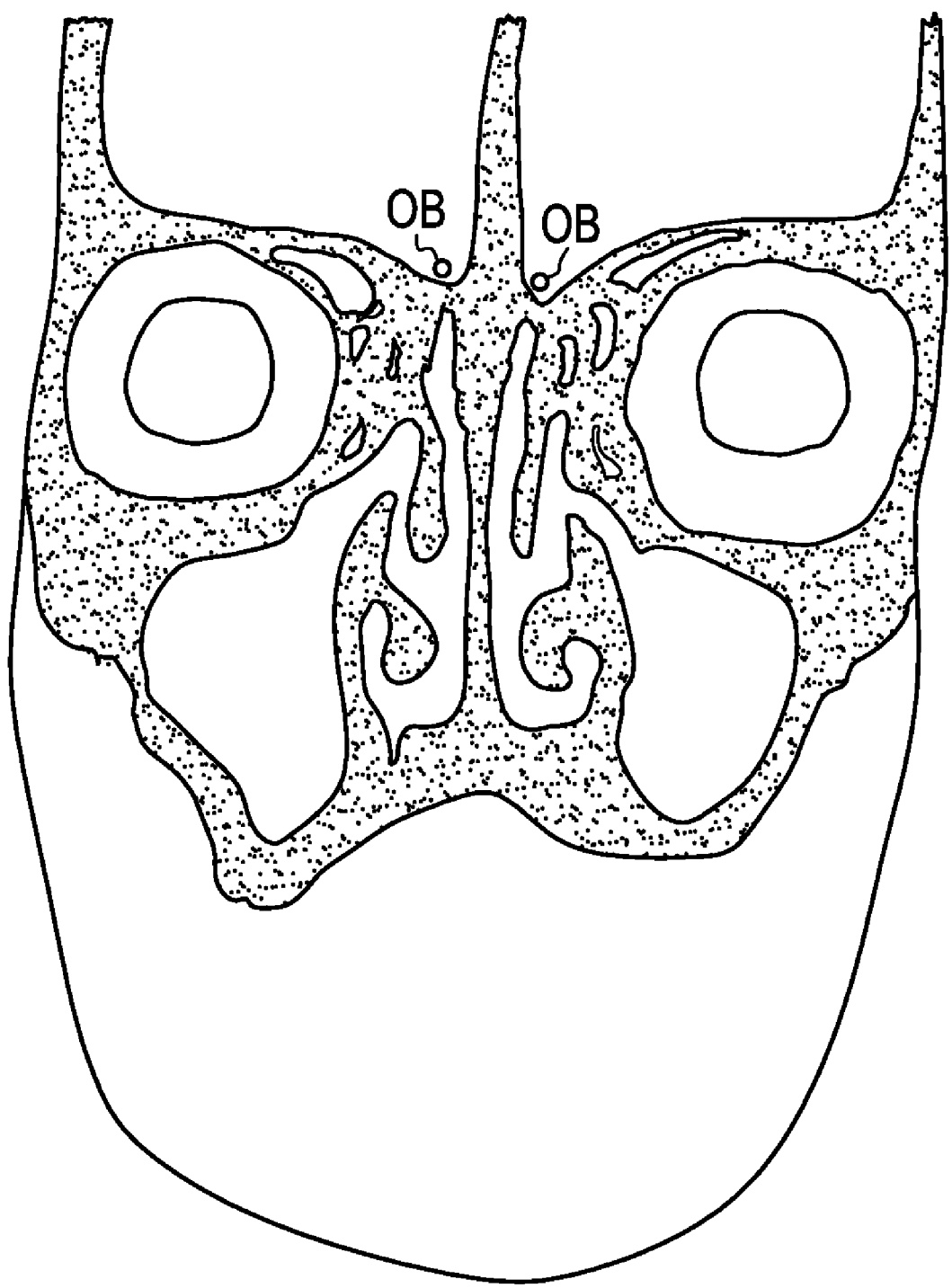
FIG. 3 discloses a frontal cross-section of the skull.

Now referring to FIG. 3, this frontal cross-section shows that the thickness cribriform plate and the olfactory bulb comprise only about two mm.

In some embodiments, lymphatic circulation ("the pump flow index") is increased by applying to the olfactory mucosa an effective amount of a compound selected from the group consisting of an NO antagonist, arachidonic acid and an antioxidant.

The present inventors have further noted that the literature is replete with references to the negative effect of nitric oxide (NO) on lymphatic vessel pumping rate. Von der Weid, *Am. J. Physiol. Heart Circ. Physiol.* 2001 June: 280(6) H2707-16 reports data consistent with the hypothesis that NO inhibits lymphatic vasoconstriction primarily by production of cGMP and activation of both cGMP- and cAMP-dependent protein kinases.

It appears that inhibition of the constitutive expression of endothelial NO synthase (eNOS) effectively increases lymphatic pumping activity. Therefore, in some embodiments, the formulation applied to the nasal lymphatics includes an inhibitor of the constitutive expression of endothelial NO synthase. In some embodiments, the inhibitor is L-NAME. Shirasawa, *Am. J. Physiol. Gastrointest. Liver Physiol*. 278: G551-G556, 2000 reports that a 15 minutes superfusion of 30 uM L-NAME into the mesenteries caused a significant ~40% increase in lymphatic pump flow index.

In some embodiments, the formulation includes an NO scavenger, such as piperazine.

In some embodiments, the formulation includes a nitrone radical scavenger, such as 2-sulfo-phenyl-N-tert-butyl nitrone (S-PBN)

It appears that inducible NOS (iNOS) does not play a role in lymphatic circulation. Louin *Neuropharmacology,* 2006, February 50(2) 182-90 reports that selective inhibition of inducible nitric oxide did not reduce cerebral edema following TBI.

The present inventors have further noted that the literature contains references to the negative effect of reactive oxygen species on lymphatic vessel pumping rate. Zawieja, *Lymphology*, 1993, Sep. 26(3) 135-42 reports upon the intense inhibition of the active lymph pump in rat mesenteric lymphatics by hydrogen peroxide. Accordingly, in some embodiments of the present invention, anti-oxidants are applied to the intranasal lymphatic vessels.

In some embodiments, the anti-oxidant is a Vitamin, wherein the Vitamin is selected from the group consisting of Vitamin A, Vitamin C and Vitamin E.

In some embodiments, the anti-oxidant is lipohilic. Preferred lipophilic anti-oxidants include retinol, lycopene, alpha-carotene, beta-carotene, alpha-tocophenol, and gamma-tocophenol.

In some embodiments, the vasoconstrictor, NO antagonist or anti-oxidant can be combined with a mucoadhesive to enhance its contact with the nasal mucosa. In some embodiments, the mucoadhesive is selected from the group consisting of a hydrophilic polymer, a hydrogel and a thermoplastic polymer. Preferred hydrophilic polymers include cellulose-based polymers (such as methylcellulose, hydroxyethyl cellulose, hydroxy propyl methyl cellulose, sodium carboxy methyl cellulose, a carbomer chitosan and plant gum.

In some embodiments, the mucoadhesive is a water-soluble high molecular weight cellulose polymer. High molecular weight cellulose polymer refers to a cellulose polymer having an average molecular weight of at least about 25,000, preferably at least about 65,000, and more preferably at least about 85,000. The exact molecular weight cellulose polymer used will generally depend upon the desired release profile. For example, polymers having an average molecular weight of about 25,000 are useful in a controlled-release composition having a time release period of up to about 8 hours, while polymers having an average molecular weight of about 85,000 are useful in a controlled-release composition having a time released period of up to about 18 hours. Even higher molecular weight cellulose polymers are contemplated for use in compositions having longer release periods. For example, polymers having an average molecular weight of 180,000 or higher are useful in a controlled-release composition having a time release period of 20 hours or longer.

The controlled-release carrier layer preferably consists of a water-soluble cellulose polymer, preferably a high molecular weight cellulose polymer, selected from the group consisting of hydroxypropyl methyl cellulose (HPMC), hydroxyethyl cellulose (HEC), hydroxypropyl cellulose (HPC), carboxy methyl cellulose (CMC), and mixtures thereof. Of these, the most preferred water-soluble cellulose polymer is HPMC. Preferably the HPMC is a high molecular weight HPMC, with the specific molecular weight selected to provide the desired release profile.

The HPMC is preferably a high molecular weight HPMC, having an average molecular weight of at least about 25,000, more preferably at least about 65,000 and most preferably at least about 85,000. The HPMC preferably consists of fine particulates having a particle size such that not less than 80% of the HPMC particles pass through an 80 mesh screen. The HPMC can be included in an amount of from about 4 wt % to about 24 wt %, preferably from about 6 wt % to about 16 wt % and more preferably from about 8 wt % to about 12 wt %, based upon total weight of the composition.

Hydrogels can also be used to deliver the vasoconstrictor, NO antagonist or anti-oxidant to the olfactory mucosa. A "hydrogel" is a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking. The hydrogels employed in this invention rapidly solidify to keep the vasoconstrictor, NO antagonist or anti-oxidant at the application site, thereby eliminating undesired migration from the site. The hydrogels are also biocompatible, e.g., not toxic, to cells suspended in the hydrogel. A "hydrogel-inducer composition" is a suspension of a hydrogel containing desired the vasoconstrictor, NO antagonist or anti-oxidant . The hydrogel-inducer composition forms a uniform distribution of inducer with a well-defined and precisely controllable density. Moreover, the hydrogel can support very large densities of inducers. In addition, the hydrogel allows diffusion of nutrients and waste products to, and away from, the inducer, which promotes tissue growth.

Hydrogels suitable for use in the present invention include water-containing gels, i.e., polymers characterized by hydrophilicity and insolubility in water. See, for instance, "Hydrogels", pages 458-459 in Concise Encyclopedia of Polymer Science and Engineering, Eds. Mark et al., Wiley and Sons, 1990, the disclosure of which is incorporated herein by reference.

In a preferred embodiment, the hydrogel is a fine, powdery synthetic hydrogel. Suitable hydrogels exhibit an optimal combination of such properties as compatibility with the matrix polymer of choice, and biocompatability. The hydrogel can include any of the following: polysaccharides, proteins, polyphosphazenes, poly(oxyethylene)-poly(oxypropylene) block polymers, poly(oxyethylene)-poly (oxypropylene) block polymers of ethylene diamine, poly (acrylic acids), poly(methacrylic acids), copolymers of acrylic acid and methacrylic acid, poly(vinyl acetate), and sulfonated polymers. Other preferred hydrogels include poly (acrylic acid co acrylamide) copolymer, carrageenan, sodium alginate, guar gum and modified guar gum.

In general, these polymers are at least partially soluble in aqueous solutions, e.g., water, or aqueous alcohol solutions that have charged side groups, or a monovalent ionic salt thereof. There are many examples of polymers with acidic side groups that can be reacted with cations, e.g., poly(phosphazenes), poly(acrylic acids), and poly(methacrylic acids). Examples of acidic groups include carboxylic acid groups, sulfonic acid groups, and halogenated (preferably fluorinated) alcohol groups. Examples of polymers with basic side groups that can react with anions are poly(vinyl amines), poly(vinyl pyridine), and poly(vinyl imidazole).

Preferred thermoplastic polmers include PVA, polyamide, polycarbonate, polyalkylene glycol, polyvinyl ether, polyvinyl ether, and polyvinyl halides, polymethacrylic acid, polymethylmethacrylic acid, methyl cellulose, hydroxypropyl cellulose, hydroxypropyl methylcellulose, and sodium carboxymethylcellulose, ethylene glycol copolymers, Other polymers that may be suitable for use as a mucoadhesive include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof For the purpose of this invention aliphatic polyesters include, but are not limited to, homopolymers and copolymers of lactide (which includes lactic acid, D-,L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$- butyrolactone, $\chi$-butyrolactone, $\epsilon$-decalactone, hydroxybutyrate, hydroxyvalerate, 1,4- dioxepan-2-one (including its dimer 1,5,8,12-tetraoxacyclotetradecane-7,14-dione), 1,5- dioxepan-2-one, 6,6-dimethyl-1,4-dioxan-2-one, 2,5-diketomorpholine, pivalolactone, $\chi,\chi$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly (ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer-based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

In some embodiments, the mucoadhseive is selected from the group consisting of poly(lactic acid) ("PLA") and poly (glycolic acid)("PGA"), and copolymers thereof.

In some embodiments, the mucoadhesive formulation includes a penetration enhancer such as sodium glycocholate, sodium taurocholate, L-lysophosphotidyl choline, DMSO and a protease inhibitor.

For delivery, there is provided a standard nose drops squeezable spray container with a long thin semi-flexible tube attached to the distal end. The outer diameter of the tube is less than a millimeter, preferably less than 0.5 mm, more preferably less than 0.25 mm. The exit hole of the tube is preferably located on the peripheral wall near the distal end of the tube so that spray exiting it can be directed upwards. There is a marker on the container that indicates when the exit hole is oriented upwards towards the cribriform plate.

Therefore, in accordance with the present invention, there is provided an intranasal spray device for increasing intranasal lymphatic flow,
 a) a hollow container having a first opening,
 b) a flexible tube having a throughbore, a side surface having a second opening, a proximal end having a third opening, and a distal end having an end surface,
 c) a formulation comprising a therapeutic agent contained within the container,
wherein the third opening of the proximal end of the tube is in fluid connection with the first opening of the hollow container, and
wherein the therapeutic agent is selected from the group consisting of an NO antagonist and an anti-oxidant.

The user directs the tube towards the medial wall of the nostril and points upwards so as to direct it medial to and over the middle nasal concha. The length of the tube is predetermined so that when the user has the shoulder of the container flush against the nostril the hole is adjacent the cribriform plate.

If there is concern about the safety of inserting a tube through a nasal passage, then the tube can also be balloon-like, so that it expands to full length upon being pressurized.

It appears that the action of the NO antagonist requires continuous infusion, and so placing the NO antagonist in a sustained release device provides such continuous delivery. Conversely, the action of the NO antagonist can be controlled by simply rinsing out the nasal cavity with water, thereby removing the sustained release of the NO antagonist.

The efficacy of the NO antagonist can be monitored by monitoring intracranial pressure.

In preferred embodiments, the formulation is applied to the olfactory mucosa. In preferred embodiments, the formulation is applied to the lymphatics located in the submucosa of the olfactory epithelium (olfactory turbinates). In preferred embodiments, the formulation is applied to the lymphatics that encircle the olfactory nerve trunks on the extracranial surface of the cribriform plate.

It is further believed that irradiation of intranasal lymphatic tissue with an effective amount of red light with also increase lymphatic circulation.

Therefore, in accordance with the present invention, there is provided a method of treating a patient having a raised intracranial pressure, comprising:
 a) irradiating a nasal lymphatic tissue of the patient with an effective amount of red light to increase lymphatic circulation.

It has been reported in the literature that red light irradiation of cells increases anti-oxidant activity and strongly deceases eNOS production. For example, Leung, *Laser Surg. Med.* 31:283-288 (2002), investigated the effect of low energy red laser after stroke in rats, and found that red light can both suppress eNO synthase activity. In particular, Leung found that irradiating a portion of the rat's brain with a 660 nm red light (average power 8.8 mW, 2.64 J/cm$^2$) reduced eNOS activity up to about 85% over that in unirradiated stroke rats, and up to about 60% over the NOS activity in normal rats. See FIG. 3 of Leung. Leung concluded that the main findings of the study was that low energy laser may be protective by suppressing the activity of NOS.

Therefore, it is reasonable to believe that red light will effect an increase in lymphatic pump activity through these same mechanisms. In fact, U.S. Pat. No. 5,640,978 ("Wong") reports_using red light laser energy to increase lymphatic circulation.

Moreover, red light may further enhance the pumping rate by decreasing the pro-oxidant activity in lymphatic vessels. According to Kamanli, *Cell Biochem. Func.* 2004, 22:53-57, catalase detoxifies hydrogen peroxide and converts lipid hydroperoxides into non-toxic alcohols, and is essential for the inhibition of inflammation related to the function of neutrophils. Romm, *Biull. Eksp. Biol. Med.* 1986 October 102 (10) 426-8 reports that laser irradiation of wounds results in a decreased chemiluminescence that is attributable to activation of catalase in the tissue fluid.

Therefore, it is believed that irradiating the TBI nasal passage with an effective amount of red light will therapeutically increase of the activity of catalase in the irradiated region, thereby attenuating the deleterious effect of hydrogen peroxide upon the pumping activity in lymphatic tissue in the TBI patient.

Similarly, according to Kamanli, supra, SOD catalyses dismutation of the superoxide anion into hydrogen peroxide. The literature repeatedly reports that red light irradiation of inactivated SOD increases its activity. For example, Vladimirov, *Biochemistry (Moscow)* 69(1) 2004, 81-90 provides a review including the photoreactivation of Cu—Zn SOD under He—Ne laser. Karu, *Laser Ther.* 1993, 5, 103-9 reports that reactive oxygen species in human blood were found to be suppressed after laser diode illumination at 660 nm, 820 nm, 880 nm and 950 nm. This affect has been attributed by other authors to the activation of SOD or catalase. Volotovskaia *Vopr Kurortol Zizioter Lech Fiz Kult* 2003 May-June(3)22-5 reports that 632 nm He—Ne laser irradiation of blood has an anti-oxidant effect as shown by activation of SOD. Ostrakhovich Vestn Ross Akad Med Nauk. 2001(5) 23-7 reports that infrared pulse laser therapy of RA patients caused an increase in SOD activity. Gorbatenkova *Biofizika,* 1988 July-August 33(4) 717-9 reports that SOD that was inactivated by hydrogen peroxide was reactivated by a 450-680 nm red light laser. Vladimirov, *Free Rad. Biol. Med.* 1988, 5(5-6) 281-6 reports the inactivation of SOD by its incubation in a low pH 5.9 solution and its subsequent reactivation by helium-neon laser light. Catalase was found to be reactivated as well. Cho, *In Vivo,* 2004, September-October 18(5) 585-91 reports on the use of low level laser therapy (LLLT) to treat knee joints that have been induced with OA by injection of hydrogen peroxide. SOD was reported to increase about 40% in the OA group as compared to controls.

Therefore, it is believed that irradiating the TBI nasal passage with an effective amount of red light will therapeutically increase of the activity of SOD in the irradiated region, thereby attenuating the deleterious effect of superoxide anion upon the pumping activity in lymphatic tissue in the TBI patient.

Preferably, the red light of the present invention has a wavelength of between about 650 nm and about 1000 nm. In some embodiments, the wavelength of light is between 800 and 900 nm, more preferably between 800 nm and 835 nm. In this range, red light has a large penetration depth, thereby facilitating its transfer to the tissue. In some embodiments, the light source is situated to irradiate adjacent tissue with between about 0.02 J/cm$^2$ and 200 J/cm$^2$ energy. Without wishing to be tied to a theory, it is believed that light transmission in this energy range will be sufficient to increase the activity of the cytochrome oxidase and anti-oxidant activity around and in the lymphatic tissue. In some embodiments, the light source is situated to irradiate target tissue with more than 10 J/cm$^2$, and preferably about 100 J/cm$^2$ energy. In some embodiments, the light source is situated to irradiate adjacent tissue with between about 0.2 J/cm$^2$ and 50 J/cm$^2$ energy, more preferably between about 1 J/cm$^2$ and 10 J/cm$^2$ energy.

In some embodiments, the light source is situated to produce an energy intensity of between 0.1 watts/cm$^2$ and 10 watts/cm$^2$. In some embodiments, the light source is situated to produce about 1 milliwatt/cm$^2$. Therefore, in some embodiments of the present invention, the therapeutic dose of red light is provided to the TBI patient on approximately a daily basis, preferably no more than 3 times a day, more preferably no more than twice a day, more preferably once a day.

In some embodiments, the red light irradiation is delivered in a continuous manner. In others, the red light irradiation is pulsed in order to reduce the heat associated with the irradiation. Without wishing to be tied to a theory, it is believed that pulsed light may be more effective in achieving the vibratory oscillation of the catalase and SOD molecules.

Figure 4C:
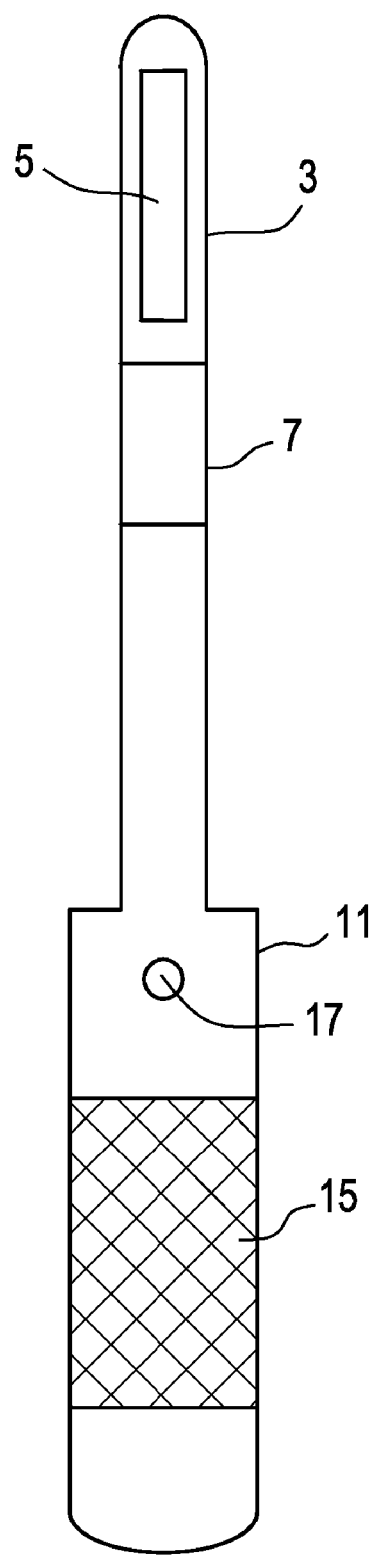

Now referring to FIGS. 4*a*-4*c*, there is provided a probe 1 for treating a neurodegenerative disease in a patient, comprising:
   a) a distal portion 3 adapted to fit within an upper portion of a nasal cavity and having a red light emitter 5 oriented towards the cribriform plate,
   b) a flexible intermediate portion 7 having an angled, narrowed portion 9,
   c) a proximal portion 11 having a handgrip 13 having a knurled surface 15 and a red light activation button 17,
   d) a red light source (not shown),
   e) a fiber optic cable (not shown) connecting the red light source and the red light emitter.

In some embodiments, the height of the distal portion is greater than its width. This allows orientation. In some embodiments, the distal portion is detachable from the remainder of the device. This allows it to be periodically cleaned by the user. In some embodiments, the tip of the distal portion is rounded in order to ease the entry of the distal portion in the nasal passage. In some embodiments, the length of the distal portion corresponds substantially to the length of the cribriform plate. This allows the red light emitter to emit light along substantially the entire porosity of the cribriform plate. In some embodiments, the length of the red light emitter corresponds substantially to the length of the cribriform plate. In some embodiments, the red light emitter is oriented to face the cribriform plate upon insertion in the nasal passage. In some embodiments, the distal portion has an upper surface oriented to face the cribriform plate upon insertion. In some embodiments, the red light emitter emits light in an arc of less than 180 degrees. In some embodiments, the red light emitter emits light substantially lateral to the longitudinal axis of the proximal portion.

In some embodiments, the narrowed portion is provided along only one axis, thereby providing preferred bending.

In some embodiments, the red light source is located in the proximal portion. In some embodiments, the red light source is located in the distal portion. In some embodiments, the red light source is operated by a battery contained within the device. In some embodiments, the red light source is operated by an electric power cord connected to the device.

In some embodiments, a light reflective surface is provided around the red light emitter to concentrate the light.

Therefore, in accordance with the present invention, there is provided a probe for treating a neurodegenerative disease in a patient, comprising:
 a) a distal portion adapted to fit within a portion of a nasal cavity and having a red light emitter,
 b) a proximal portion having a handgrip having a knurled surface and a red light activation button, and
 c) a red light source.

In some embodiments, the distal portion of the probe has a thickness of less than 1 mm, preferably less than 0.1 mm, in order to reduce irritation of the nasal cavity.

In some embodiments, the distal portion of the probe is a thin fiber optic cable that has reflective material dispersed therein so that light will disperse in all directions therefrom.

In some embodiments, prior to probe insertion, a painkiller is sprayed into the nasal cavity so that the patient may more easily tolerate the insertion of the probe into the nasal cavity.

In preferred embodiments, the red light irradiates the olfactory mucosa with an effective amount of red light. In preferred embodiments, the red light irradiates the cribriform plate with an effective amount of red light. In preferred embodiments, the red light irradiates the lymphatics located in the submucosa of the olfactory epithelium (olfactory turbinates) with an effective amount of red light. In preferred embodiments, the red light irradiates the lymphatics that encircle the olfactory nerve trunks on the extracranial surface of the cribriform plate with an effective amount of red light.

In some embodiments, the irradiation is accomplished by inserting a red light emitting probe into the nasal cavity and activating the red light probe to emit red light. In some embodiments thereof, the red light emitting probe is placed adjacent the olfactory mucosa. In some embodiments thereof, the red light emitting probe is placed adjacent the lymphatics located in the submucosa of the olfactory epithelium (olfactory turbinates). In some embodiments thereof, the red light emitting probe is placed adjacent the lymphatics that encircle the olfactory nerve trunks on the extracranial surface of the cribriform plate In some embodiments of the present invention, the patient having a raised intracranial pressure has a traumatic brain injury (TBI). In some embodiments of the present invention, the patient having a raised intracranial pressure has a stroke. In some embodiments of the present invention, the patient having a raised intracranial pressure has hydrocephalus. In some embodiments of the present invention, the patient having a raised intracranial pressure has Alzheimer's Disease (AD).

We claim:

1. A method of treating a patient having a raised intracranial pressure, comprising:
 a) irradiating a nasal lymphatic tissue of the patient with an amount of red light of between about 0.02 J/cm$^2$ and 200 J/cm$^2$ to increase lymphatic circulation.

2. The method of claim 1 wherein the patient has hydrocephalus.

3. The method of claim 1 wherein the patient has a stroke.

4. The method of claim 1 wherein the patient has traumatic brain injury.

5. The method of claim 1 wherein the irradiation is accomplished by inserting a red light emitting probe into a nasal cavity and activating the red light probe to emit red light.

6. The method of claim 5 wherein the red light emitting probe is placed adjacent an olfactory mucosa.

7. The method of claim 5 wherein the red light emitting probe is placed adjacent lymphatics located in a submucosa of an olfactory epithelium.

8. The method of claim 5 wherein the red light emitting probe is placed adjacent lymphatics that encircle olfactory nerve trunks on an extracranial surface of a cribriform plate.

9. The method of claim 1 wherein a pain-killer is sprayed into a nasal cavity of the patient prior to irradiation.

10. The method of claim 1 wherein the amount of red light is between about 0.2 J/cm$^2$ and 50 J/cm$^2$.

11. The method of claim 1 wherein the amount of red light is of between about 1 J/cm$^2$ and 10 J/cm$^2$.

* * * * *